(12) United States Patent
Greenberg et al.

(10) Patent No.: US 11,006,225 B2
(45) Date of Patent: May 11, 2021

(54) AUDITORY DEVICE ASSEMBLY

(71) Applicant: EARTEX LIMITED, London (GB)

(72) Inventors: David Greenberg, London (GB); Clive Taylor, Hertfordshire (GB)

(73) Assignee: EARTEX LIMITED, London (GB)

( * ) Notice: Subject to any disclaimer, the term of this patent is extended or adjusted under 35 U.S.C. 154(b) by 0 days.

(21) Appl. No.: 16/348,692

(22) PCT Filed: Nov. 10, 2017

(86) PCT No.: PCT/GB2017/053402
§ 371 (c)(1),
(2) Date: May 9, 2019

(87) PCT Pub. No.: WO2018/087566
PCT Pub. Date: May 17, 2018

(65) Prior Publication Data
US 2019/0289409 A1    Sep. 19, 2019

(30) Foreign Application Priority Data
Nov. 11, 2016 (GB) ........................... 1619160

(51) Int. Cl.
*H04R 25/00* (2006.01)
*H04R 29/00* (2006.01)
(Continued)

(52) U.S. Cl.
CPC ........... *H04R 25/505* (2013.01); *A61B 5/121* (2013.01); *A61B 5/125* (2013.01); *A61B 5/7264* (2013.01);
(Continued)

(58) Field of Classification Search
CPC ........ H04R 25/00; H04R 29/00; H04R 25/55; H04R 25/558; H04R 2225/49; H04R 2460/01
(Continued)

(56) References Cited

U.S. PATENT DOCUMENTS 4,471,171 A    9/1984  Kopke et al.
9,414,173 B1    8/2016  Hou
(Continued)

FOREIGN PATENT DOCUMENTS

DE    4128172    3/1993
WO    2007052186    5/2007
(Continued)

OTHER PUBLICATIONS

International Search Report and Written Opinion dated Jan. 15, 2018, from International Application No. PCT/GB2017/053402, 9 pages.
(Continued)

*Primary Examiner* — Suhan Ni
(74) *Attorney, Agent, or Firm* — Meunier Carlin & Curfman LLC (57) ABSTRACT

An auditory device assembly (1) comprises an earpiece (3) having an audio output device (7) for an ear (9) of a user and an audio processing unit (11, 33). The audio processing unit (11, 33) has a hearing-test mode and an audio streaming mode. In the hearing test mode the audio processing unit (11, 33) is arranged to determine at least one ear characteristic of the ear of the user based on at least one hearing test. In the audio streaming mode the audio processing unit (11, 33) is arranged to output an audio stream via the audio output device (7). The audio processing unit (11, 33) is arranged to
(Continued)

adjust the output of the audio stream in the audio streaming mode based on the at least one ear characteristic determined in the hearing-test mode.

24 Claims, 8 Drawing Sheets

(51) Int. Cl.
    *A61B 5/12*     (2006.01)
    *A61B 5/00*     (2006.01)

(52) U.S. Cl.
    CPC ......... *H04R 25/554* (2013.01); *H04R 25/558* (2013.01); *H04R 25/604* (2013.01); *H04R 25/70* (2013.01); *A61B 2562/0204* (2013.01); *H04R 2225/55* (2013.01); *H04R 2430/01* (2013.01)

(58) Field of Classification Search
    USPC ........................... 381/60, 312, 315, 317–318
    See application file for complete search history.

(56) References Cited

U.S. PATENT DOCUMENTS

| | | |
|---|---|---|
| 2004/0028250 A1 | 2/2004 | Shim |
| 2004/0234089 A1* | 11/2004 | Rembrand ............. H04R 25/30 381/312 |
| 2007/0076909 A1 | 4/2007 | Roeck et al. |
| 2008/0219486 A1 | 9/2008 | Goldstein et al. |
| 2010/0119093 A1 | 5/2010 | Uzuanis et al. |
| 2014/0247952 A1 | 9/2014 | Goldstein |
| 2014/0309549 A1 | 10/2014 | Selig et al. |
| 2014/0314261 A1 | 10/2014 | Selig et al. |

FOREIGN PATENT DOCUMENTS

| | | |
|---|---|---|
| WO | 2008061260 | 5/2008 |
| WO | 2011109212 | 9/2011 |
| WO | 2012016527 | 2/2012 |

OTHER PUBLICATIONS

International Preliminary Report on Patentability dated Jan. 4, 2019, from International Application No. PCT/IB2017/053402, 19 pages.

Written Opinion dated Oct. 8, 2018, from International Application No. PCT/GB2017/053402, 5 pages.

Search Report under Section 17(5) and Examination Opinion dated Jan. 17, 2018, from GB application No. 1619160.3, 4 pages.

* cited by examiner

AUDITORY DEVICE ASSEMBLY

TECHNICAL FIELD

This disclosure relates to an auditory device assembly, an earpiece, an audio processing unit and a method of adjusting audio based on an ear characteristic of an ear of a user.

BACKGROUND

Typically, hearing tests are carried out by a skilled clinician using specialised equipment. Thus, when a person has an issue with their hearing, they are required to visit the clinician for a hearing test to be conducted.

After a hearing test is completed, the results of the hearing test are analysed and, in some cases, a hearing-aid is prescribed. The prescribed hearing-aid device will be tuned based on the results of the hearing-test, with the aim of alleviating the hearing problems of the individual.

This hearing testing and tuning process is undesirable for many reasons. For instance, the process can be time consuming and costly. Another drawback is that, if a person's hearing issues change, it may be some time before their hearing-aid device can be re-tuned to compensate for any such changes. Therefore, it would be desirable to provide a more efficient and convenient hearing test and hearing-aid tuning processes.

Another example of a drawback relating to existing auditory devices is that, in general, earphones are designed to have only one audio output profile. However, this is undesirable because each person has a different hearing profile, as different people hear sounds differently and may have different sensitivities to different frequencies. Therefore, one particular earphone may be acceptable for one person, but may be entirely inappropriate for another individual. Therefore, it would be desirable to provide an auditory device that can be optimised for individual users.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

According to one aspect of the invention there is provided an auditory device assembly comprising: an earpiece having an audio output device for an ear of a user; and an audio processing unit having: a hearing-test mode in which the audio processing unit is arranged to determine at least one ear characteristic of the ear of the user based on at least one hearing test; and an audio streaming mode in which the audio processing unit is arranged to output an audio stream via the audio output device; wherein the audio processing unit is arranged to adjust the output of the audio stream in the audio streaming mode based on the at least one ear characteristic determined in the hearing-test mode.

According to another aspect of the invention there is provided an earpiece comprising: an audio output device, for an ear of a user, communicatively connected to an audio processing unit having: a hearing-test mode in which the audio processing unit is arranged to determine at least one ear characteristic of the ear of the user based on at least one hearing test; and an audio streaming mode in which the audio processing unit is arranged to output an audio stream via the audio output device; wherein the audio processing unit is arranged to adjust the output of the audio stream in the audio streaming mode based on the at least one ear characteristic determined in the hearing-test mode.

According to another aspect of the invention there is provided an audio processing unit having: an audio streaming mode in which the audio processing unit is arranged to output an audio stream via an audio output device of an earpiece for an ear of a user; a hearing-test mode in which the audio processing unit is arranged to determine at least one ear characteristic of the ear of the user based on at least one hearing test; and wherein the audio processing unit is arranged to adjust the output of the audio stream in the audio streaming mode based on the at least one ear characteristic determined in the hearing-test mode.

According to another aspect of the invention there is provided a method comprising: determining at least one ear characteristic of an ear of a user, using an audio processing unit in a hearing-test mode; outputting an audio stream via an audio output device of an earpiece for an ear of a user, using the audio processing unit in an audio streaming mode; and adjusting the output of the audio stream in the audio streaming mode, using the audio processing unit based on the at least one ear characteristic determined in the hearing-test mode.

According to another aspect of the invention there is provided a computer program comprising code portions which when loaded and run on a computer cause the computer to execute a method as described above.

BRIEF DESCRIPTION OF THE DRAWINGS

Embodiments of the invention will be described, by way of example, with reference to the following drawings, in which.

DETAILED DESCRIPTION

Described herein is an auditory device assembly which has a hearing-test mode in which an audio processing unit is arranged to determine an ear characteristic; and an audio streaming mode in which the audio processing unit is arranged to output an audio stream, which is adjusted based on the ear characteristic. Thus, a user can administer a hearing-test using the audio processing unit, in order to determine a characteristic of their ears. Then, this characteristic can be used to adjust the audio stream from the audio processing unit in the audio streaming mode. This provides a single assembly which a user can operate to tune the auditory device assembly without having to visit a clinician. Since the audio processing unit conducts the hearing test and the audio streaming, the auditory device assembly can be tuned immediately after the hearing-test. This avoids the need to wait for results to be processed by a separate unit. Furthermore, a user can use the auditory device assembly to customise the audio stream based on at least one characteristic of their ears.

The audio processing unit may be arranged, in the hearing-test mode, to determine a plurality of ear characteristics based on the at least one hearing test. In addition, the audio processing unit may be arranged, in the hearing-test mode, to determine at least one, or a plurality of, ear characteristics based on a plurality of hearing tests.

The audio processing unit may be able to determine an ear characteristic of the user's ear more accurately by detecting a response to an audio test signal. For example, an audio test signal with a pre-defined frequency and amplitude may be output to the user's ear via an audio output device. The assembly may then detect a response by receiving an input from the user indicating that the audio test signal has been heard. This allows the audio processing unit to determine that the user is able to hear that particular sound frequency at a particular amplitude. This information can be used to adjust the output of the audio stream in the audio streaming mode, in order to optimise the user's hearing experience.

The audio processing unit may be arranged to output a plurality of pre-defined audio test signals via the audio output device, in the hearing test mode. In addition, the audio processing unit may be arranged to determine at least one characteristic of the ear of the user based on a response, or responses, to the plurality of pre-defined audio test signals.

Healthy ears emit sounds called Otoacoustic Emissions (OAEs). These OAEs are produced by the outer hairs of the cochlear in the inner ear. Generally, there are two types of OAEs: Spontaneous Otoacoustic Emissions (SOAEs) and Evoked Otoacoustic Emissions (EOAEs). SOAEs are emitted without external stimulation of the ear, whilst EOAEs are emitted when the ear is subject to external stimulation. The OAEs emitted by the ear of a user indicate characteristics of that user's ear.

The auditory device assembly may be provided with an ear-microphone which can detect sound emitted by the user's ear. Therefore, it is possible to detect OAEs emitted by the user's ear. This allows the device to determine a characteristic based on the OAEs, which in turn can be used to adjust the audio stream, in order to optimise the user's hearing experience.

Figure 1:
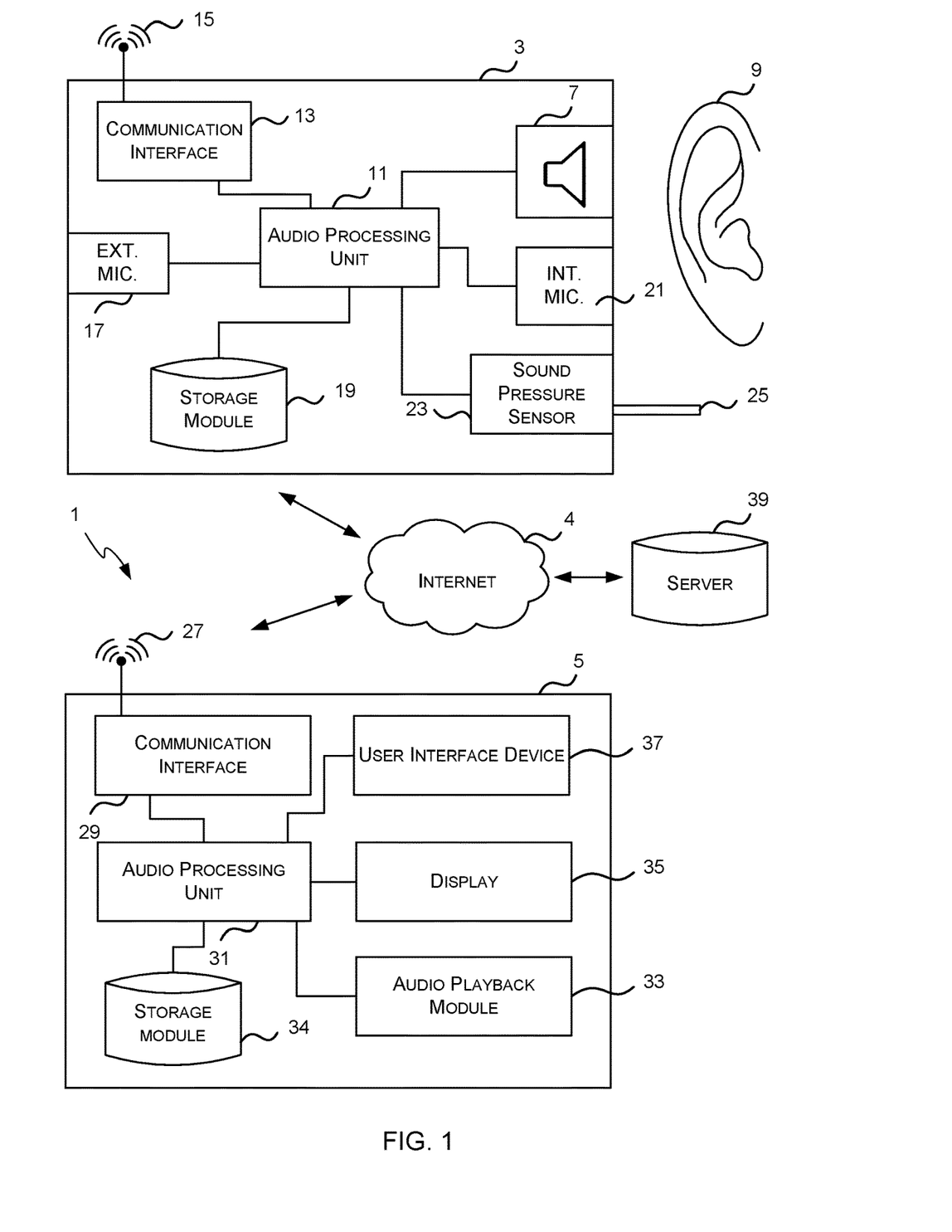
FIG. 1 schematically shows the basic general architecture of an auditory device assembly.

Referring to FIG. 1, there is an auditory device assembly 1 comprising an earpiece 3 which is communicatively connected to a computing device 5. The earpiece 3 is arranged to be worn over and/or inside a user's ear 9.

Only a single earpiece 3 is shown in FIG. 1, but preferably the auditory device assembly 1 is provided with a pair of earpieces 3, one for each ear 9 of the user. In the illustration the earpiece 3 is shown schematically. However, the earpiece 3 may be any form of listening device such as a headphone, an earphone or an earbud. In this example, the computing device 5 is a smartphone. However, it will be appreciated that any other type of suitable computing device 5 may be used.

The earpiece 3 comprises an audio output device 7, such as a speaker, which is arranged to output various types of audio from different sources. The audio output device 7 is controlled by an audio processing unit 11 of the earpiece 3. The audio processing unit 11 can receive signals from an antenna 15 through a communication interface 13. These signals are processed by the audio processing unit 11 and output by the audio output device 7.

The audio processing unit 11 is also connected to an external microphone 17, which receives sound signals from the environment outside the earpiece 3. These sound signals can be processed by the audio processing unit 11 and output by the audio output device 7. The audio processing unit 11 may be a computer processor.

The earpiece 3 further comprises an internal microphone 21. In one example, the microphone 21 is arranged to be located at least partially inside the ear 9 when the earpiece is in use. However, in another example, the microphone is arranged to be located outside the ear 9. The internal microphone 21 is used to conduct a hearing test for the ear 9 of the user, in order to determine at least one ear characteristic of the user's ear 9. This hearing test will be described in greater detail below.

The ear characteristic may represent the sensitivity of the ear 9 to at least one frequency. This ear characteristic can be stored at a storage device 19 at the earpiece 3, so that the audio processing unit 11 can adjust the audio stream based on the ear characteristic. In one example, the audio processing unit 11 is arranged to adjust the audio stream output via the audio output device based on the sensitivity of the ear 9 to certain frequencies, so that frequencies to which the ear 9 is less sensitive are amplified and/or frequencies to which the ear 9 is more sensitive are attenuated. In this way, the earpiece 3 can optimise the audio stream for an individual user's ear 9.

The earpiece 3 also includes a sound pressure sensor 23 and a probe 25. The probe 25 is arranged to be inserted at least partially inside the ear 9 when the earpiece 3 is in use. This allows the sensor 23 to measure the sound pressure level within the ear 9. The sound pressure sensor 23 and the probe 25 are used to conduct another hearing test in order to determine an ear characteristic, which again can be used to optimise the audio stream.

The audio processing unit 11 is arranged to operate in a hearing test mode and an audio streaming mode. In the hearing test mode, the audio processing unit 11 is arranged to determine at least one ear characteristic of the ear 9 based on a hearing test. In the audio streaming mode, the audio processing unit is arranged to output an audio stream via the audio output device 7, where the audio stream is adjusted based on the at least one ear characteristic.

The computing device 5 also comprises an antenna 27 and communication interface 29. The antennas 15, 27 and the communication interfaces 13, 29 are used to establish a wireless connection between the earpiece 3 and the computing device 5, so that they can communicate with one another. In this example, the earpiece 3 and the computing device 5 communicate wirelessly with one other, for instance, via Bluetooth® or via Wi-Fi. However, the earpiece 3 and the computing device 5 may also communicate with one another via any other suitable connection, such as via a wired connection.

The computing device 5 also has an audio processing unit 31, which performs a similar function as the audio processing unit 11 of the earpiece 3. The functions of the audio processing unit 11 of the earpiece 3 and the audio processing unit 31 of the computing device 5 may be shared between the audio processing units 11, 31. The audio processing unit may be a computer processor.

The audio processing unit 31 at the computing device 5 can be used to conduct hearing tests for determining an ear characteristic of the user's ear 9 also. The audio processing unit 31 can also be used for transmitting audio signals to the audio output device 7 via the antennas 15, 27 and communications interfaces 13, 29.

The computing device 5 further comprises an audio playback module 33, which is arranged to interface with the audio processing unit 31. The audio playback module 33 may be, for instance, a digital music player or a music streaming application.

The audio playback module 33 is arranged to communicate with the earpiece 3 with the audio processing units 11, 31, communication interfaces 13, 31 and antennas 15, 27 in order to output music, or any other audio, via the audio output device 7. There is also a storage module 34 at the computing device 5, which may be used for storing audio for output by the earpiece 3. The storage module 34 may also be used to store ear characteristics of the user's ear 9.

The computing device 5 also includes a display 35 and a user interface device 37. In this example, the display 35 and the user interface 37 are integrated together in the form of a touch-screen display of the computing device 5.

The earpiece 3 and the computing device 5 may also be connected to a communications network, such as the Internet 4. In addition, the earpiece 3 and computing device 5 may be connected to a server 39, for instance via the Internet 4, which may be used for storing ear characteristics and/or audio for output via the earpiece 3.

Figure 2:
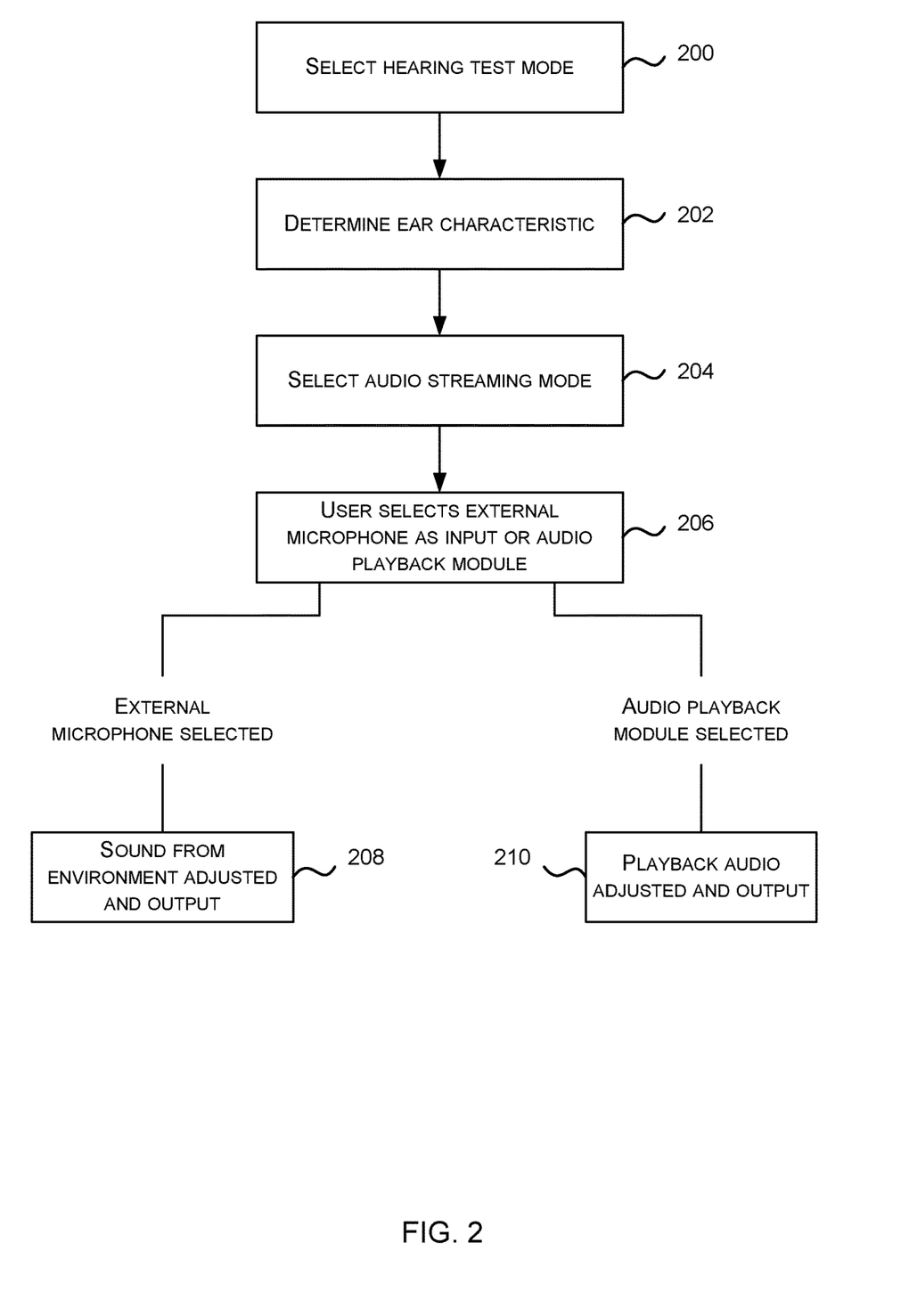
FIG. 2 shows a flow chart illustrating a method of adjusting audio based on an ear characteristic.

FIG. 2 shows a flow chart illustrating a method of adjusting an audio stream output via the earpiece 3 based on an ear characteristic of the user's ear 9. In step 200, the user selects the hearing test mode of the audio processing unit 11, 31. In order to do this, the user interacts with the user interface device 37 to activate a hearing test application at the computing device 5.

In step 202, the audio processing unit 11, 31 determines at least one ear characteristic of the user's ear 9 by carrying out at least one hearing test. Different hearing tests that may be conducted by the audio processing unit 11, 31 will be described in greater detail below. The ear characteristic can be stored at a storage module 19, 34 at the earpiece 3, the computing device 5 or the server 39.

In step 204, the user selects the audio streaming mode of the audio processing unit 11, 31. In order to do this, the user interacts with the user interface device 37 to activate an audio streaming application at the computing device 5. In this example, the hearing test application and the audio streaming application are described as separate applications. However, the functionality of each of these applications may be integrated into a single application at the computing device 5.

In step 206, the user can select either the external microphone 17 or the audio playback module 33 as the preferred source of audio. If the user selects the external microphone 17, the method proceeds to step 208. On the other hand, the user may select the audio playback module 33 as the preferred source of audio, in which case the method proceeds to step 210. In this example the audio playback module 33 is a digital music player. However, any other type of suitable music streaming application may be used. Steps 200-204 may be carried out once or many times, the same applies to steps 206-210.

In step 208, the external microphone 17 receives sound from the environment outside of the earpiece 3 and replays the received sound, in real-time, via the audio output device 7. Before, replaying the sound, the audio stream is adjusted based on the ear characteristic determined and stored in the hearing test mode. This allows the auditory device assembly 1 to optimise the user's hearing of sound in their environment.

In step 210, the audio playback module 33 transmits audio for output via the audio output device 7. Here the signals are transmitted via the audio processing units 11, 31, the communication interfaces 13, 29, and the antennas 15, 27. However, it will be appreciated that a wired communication mechanism could be used instead.

Before, replaying the audio transmitted by the audio playback module 33, the audio is adjusted based on the ear characteristic determined in the hearing test mode. This allows the auditory device assembly 1 to optimise the user's hearing of live or pre-recorded music.

Figure 3:
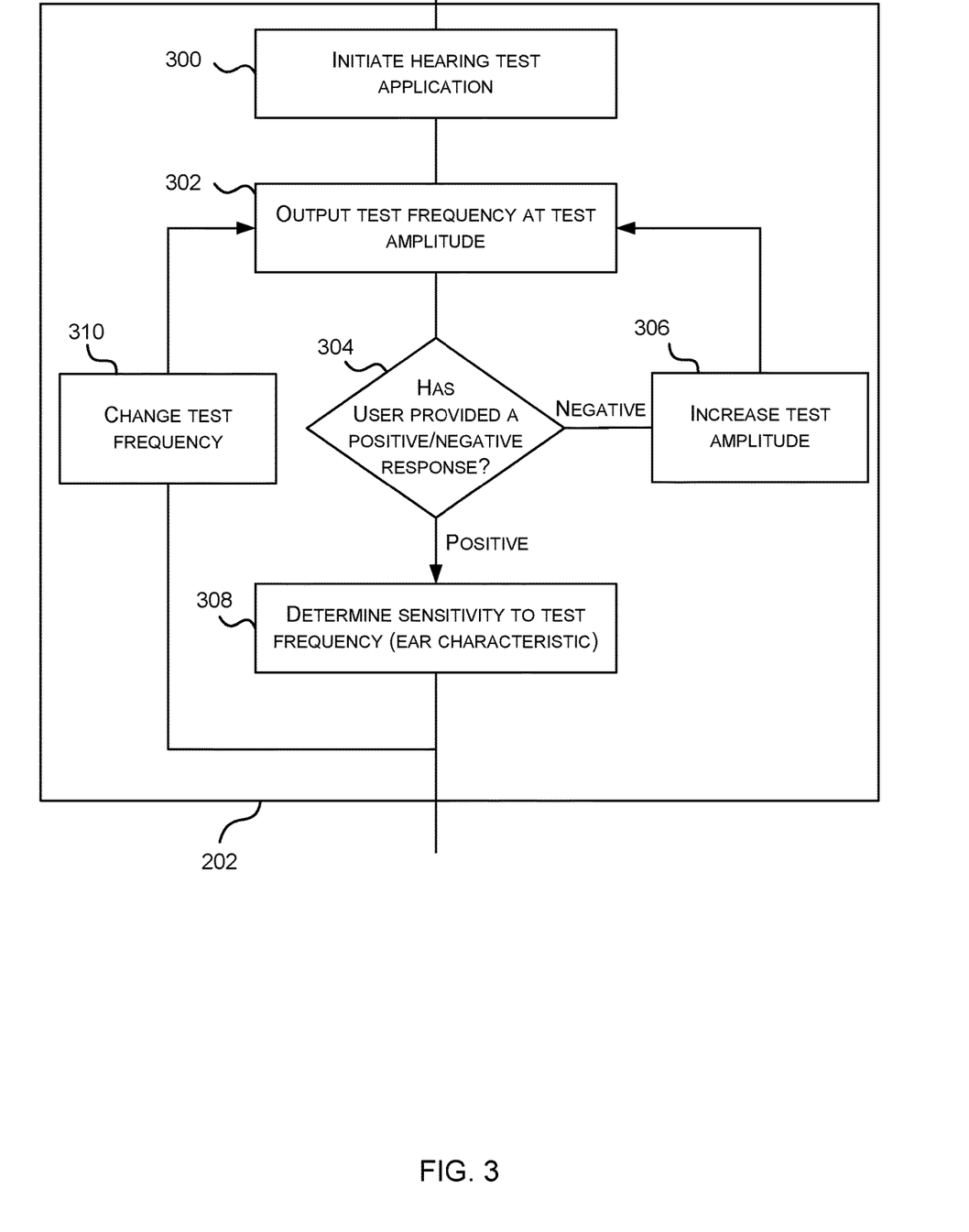
FIG. 3 shows a flow chart illustrating a method of determining an ear characteristic.

FIG. 3 shows a flow chart illustrating a more detailed example of the method in step 202 of FIG. 2 for determining an ear characteristic. In step 300, the user initiates the hearing test application using the user interface 37 and display 35. In step 302, the audio processing unit 11, 31 causes the audio output device 7 to output a first pre-defined audio test signal. The first pre-defined audio test signal has a pre-defined frequency and amplitude. In step 304, the display 35 prompts the user to provide a positive or a negative response via the user interface device 37. A positive response indicates that the user can hear the first test signal, whilst a negative response, or a lack of a response perhaps after a particular time period, indicates that the user cannot hear the first test signal.

If the user cannot hear the first test signal and a response is not received at the user interface, the method proceeds to step 306 in which the amplitude of the first test signal is increased. The method repeats steps 302-306 until the user interface device 37 receives a response from the user indicating that the test signal has been heard.

Once the user has indicated that they have heard the test signal, the method proceeds to step 308 in which the audio processing unit 11, 31 determines an ear characteristic of the ear. In this example, the ear characteristic determined is the sensitivity of the user's ear 9 to the frequency of the test signal. For instance, this sensitivity may be recorded as the minimum amplitude at which the user is able to hear a particular frequency. This minimum amplitude may indicate that it is necessary to adjust the audio stream output in the audio streaming mode, so that audio signals at this frequency are either amplified or attenuated depending on whether the user is less or more sensitive to that particular frequency.

After the ear characteristic has been determined in step 308, the method proceeds to step 310 in which the frequency of the test signal is changed. Then steps 302-308 are repeated in order to determine another ear characteristic of the ear, which in this case may be the user's sensitivity to the new frequency.

Steps 302-310 may be repeated for a range of test frequencies. In this way, the auditory device assembly 1 is able to build a hearing profile for the user. Then, audio stream output in the audio streaming mode can be adjusted accordingly in order to optimise the user's hearing experience.

Figure 4:
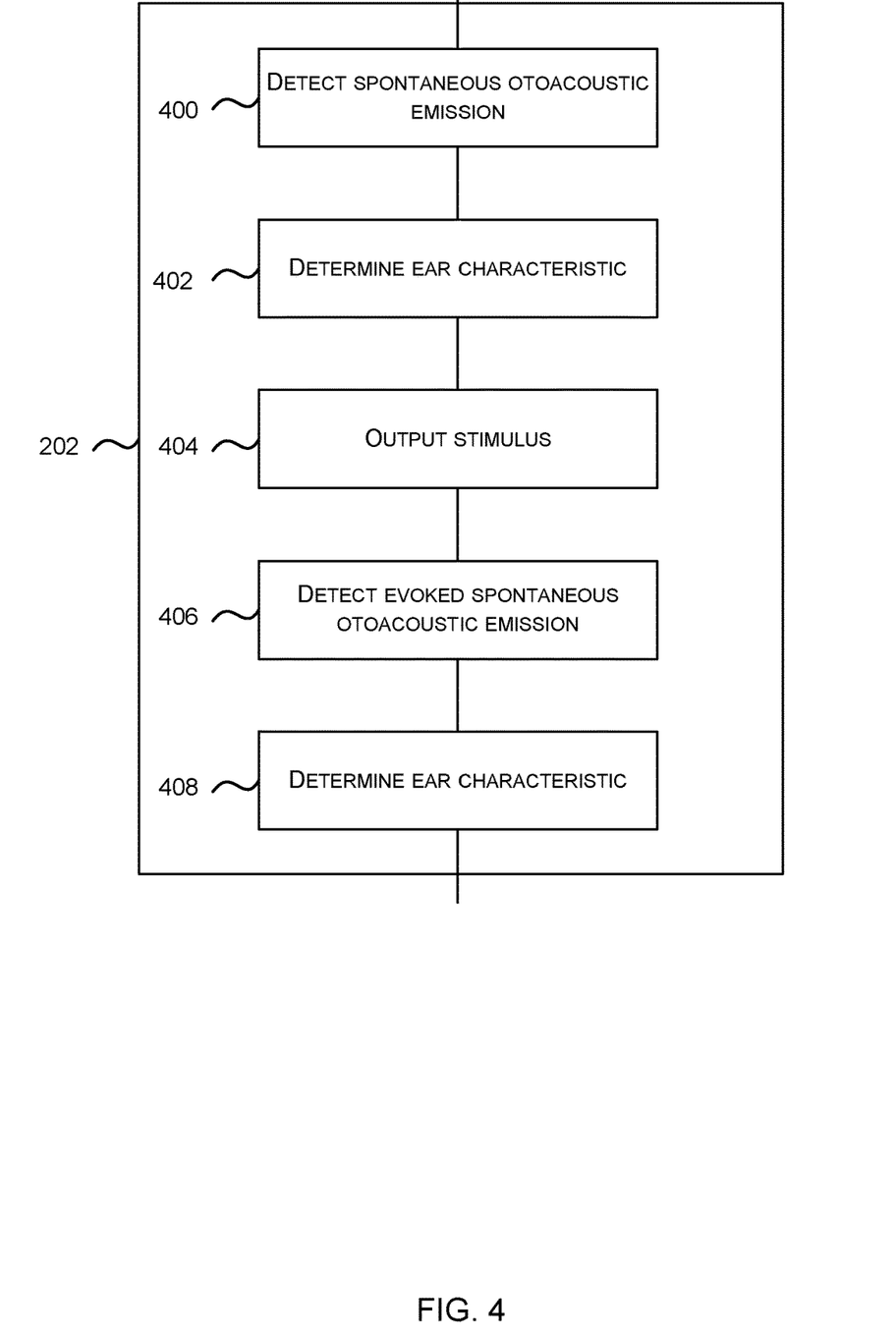
FIG. 4 shows a flow chart illustrating a method of determining an ear characteristic based on otoacoustic emissions.

FIG. 4 shows a flow chart illustrating an alternative example of the method in step 202 of FIG. 2 for determining an ear characteristic. This method of determining an ear characteristic relies on detecting Otoacoustic Emissions (OAEs) emitted by ear 9 of the user.

OAEs are sounds given off by the inner ear as a result of an active cellular process. When a soundwave enters the ear canal it is transmitted to the fluid of the inner ear via the middle ear bones. The air borne vibrations are converted into fluid borne vibrations in the cochlea. The fluid borne vibrations in the cochlea result in the outer hair cells producing a sound that echoes back into the middle ear. Outer hair cell vibrations can be induced by either external sound waves (EOAEs) or internal mechanisms (SOAEs).

People with normal hearing produce OAEs. However, those with hearing loss greater than 25-30 decibels (dB) generally do not produce OAEs. Studies have shown that OAEs disappear after the inner ear has been damaged, so OAEs can be used as a measure of inner ear health.

The primary purpose of otoacoustic emission (OAE) tests is to determine cochlear status, specifically hair cell function. It also builds up a picture of the conductive mechanism characteristics from the ear canal to the outer hair cells (OHC) of the cochlea over the hearing range of frequencies. This includes proper forward and reverse transmission, no blockage of the external auditory canal, normal tympanic membrane (eardrum) movement, and a functioning impedance matching system normally checked by impedance audiometry.

The middle ear matches the acoustic impedance between the air and the fluid, thus maximizing the flow of energy from the air to the fluid of the inner ear. Impairment in the transmission of sound through the middle ear creates a conductive hearing loss which can be compensated by increasing the amplification of sounds entering the ear canal. Therefore, more energy is needed for the individual with a conductive hearing loss to hear sound, but once any audio is loud enough and the mechanical impediment is overcome, the ear works in a normal way. OAE results in this case would typically show non-frequency specific hearing loss in the form of reduced amplitudes above the noise floor across the frequency range of hearing.

The outer hair cells (OHC) of the cochlea of the inner ear perform a resonating/amplifying role, which generate the electro-physical OAE responses. Present OAEs at the required threshold would indicate normal OHC functionality at those measured frequencies equating to normal hearing sensitivity. Any gaps in normal hearing sensitivity would need more complex adjustments such as frequency selective boosting of sound waves to the neighbouring functional outer hair cells in the case of dead regions of the cochlea.

OAEs in general provide reliable information on the ear's auditory pathway characteristics which can also be a significant help in preventing noise related hearing loss. OAEs can provide the means to monitor a patient for early signs of noise related hearing damage. Excessive noise exposure affects outer hair cell (OHC) functionality, so OAEs can be used to detect this. An OAE evaluation can give a warning sign of outer hair cell damage before it is evident on an audiogram. OAEs are more sensitive in detecting cochlear dysfunctions, since the outer hair cells are the first structure of the inner ear to be damaged by external agents, even before the record of changes in audiometric thresholds There are two types of OAE: Spontaneous Otoacoustic Emissions (SOAEs) and Evoked Otoacoustic Emissions (EOAEs). SOAEs are sounds that are emitted from the ear without external stimulation. On the other hand, EOAEs are sounds emitted from the ear in response to external stimulation.

In step 400 the internal microphone 21 is used to detect SOAEs emitted by the user's ear 9. In this step, the audio output device 7 does not provide any stimulus to the ear 9. Once the internal microphone 21 has attempted to detect any SOAEs, the method proceeds to step 402 in which an ear characteristic is determined based on the SOAEs, or lack thereof.

Spontaneous otoacoustic emissions (SOAEs) can be considered as continuously evoking otoacoustic emissions which provide supplementary information on the ear's auditory pathway characteristics. Accordingly, SOAEs are ideally suited to monitoring the user's hearing abilities during quiet periods to identify the onset of any hearing impairment without any user cooperation or awareness of the monitoring being necessary.

Spontaneous otoacoustic emissions typically show multiple narrow frequency spikes above the noise floor indicating normal functionality. An attenuation of these spikes over time could indicate impending noise related hearing impairment which may become permanent unless appropriate action is taken. The attenuation of these spikes may be recorded as an ear characteristic, and audio output can be adjusted accordingly, for instance, by increasing amplitude of audio output at these frequencies.

In step 404, the audio output device 7 outputs an audio test signal as a stimulus to the ear 9. The stimulus is arranged to cause the ear 9 to emit an EOAE, which is detected in step 406 if any EOAEs are emitted. Then, in step 408, an ear characteristic is determined based on the EOAE, or lack thereof. In some examples, the results of the SOAE detection in step 400, may be used as a basis for activating specific EOAE tests in steps 404 and 406. Such results may be, for example, changes in the user's SOAE profile, which may be determined from the results of the SOAE detection in step 400.

There are a number of different types of audio test signal that can be used as a stimulus to the ear 9 when attempting to detect EOAEs in step 404. Evoked otoacoustic emissions can be evoked using a variety of different methods.

In one method, a pure-tone stimulus is output and stimulus frequency OAEs (SFOAEs) are measured during the application of the pure-tone stimulus. The SFOAEs are detected by measuring the vectorial difference between the stimulus waveform and the recorded waveform, which consists of the sum of the stimulus and the OAE.

In another method, a click, a broad frequency range, a tone burst or a brief duration pure tone is output and transient evoked OAEs (TEOAEs or TrOAEs) are measured. The evoked response from a click covers the frequency range up to around 4 kHz, while a tone burst will elicit a response from the region that has the same frequency as the pure tone.

In another method, distortion product OAEs (DPOAEs) are evoked by outputting a pair of primary tones ($f_1$ and $f_2$). The corresponding DPOAEs are measured to determine an ear characteristic.

The pair of primary tones of similar intensity have a frequency ratio which typically lies at 1:2 from which strong distortion products (DP) should be detected at $2f_1-f_2$ and at $2f_2-f_1$, where $f_2$ is the higher frequency tone.

EOAEs measure the conductive mechanism characteristics of the ear including the integrity of the outer hair cells (OHC) which can be damaged by exposure to high levels of noise. The steepness of phase roll-off from stimulus-frequency OAEs (SFOAE) is also believed to indicate the true frequency selectivity of single fibres of the human auditory nerve that represent the stimulus input to auditory brain centres. This may help in compensating for dead regions of the cochlea by selectively elevating the magnitude of neighbouring (sideband) frequencies to supplement the missing ones.

An alternate method could be to utilise RF frequency mixing techniques to synthesise the missing frequency in the auditory (neural) centre by mixing the neural-electrical energy of two frequencies where the upper product lies towards the limit of normal hearing range and the lower product equates to the damaged area of the cochlea, ie: $\cos(\omega_{RF}\cdot t)^*\cos(\omega_{LO}\cdot t)=0.5\{\{\cos[(\omega_{RF}-\omega_{LO})t]+\cos[(\omega_{RF}+\omega_{LO})t]\}$. In this method, the non-linear function of the cochlear will need to be taken into account.

EOAE measurements provide frequency specific information about the users's hearing ability in terms of establishing whether auditory thresholds are within normal limits, which is important for hearing aid settings, and for diagnosing sensory or conductive hearing impairment which can lead to problems understanding speech in the presence of background noise.

Conventional techniques such as air- and bone-conduction pure-tone audiometry and simple speech audiometry are not always as reliable. Tuning the hearing device from OAE data as described previously to compensate for any hearing impairment and/or perceived deficiencies needs to account for the acoustic properties of the ear canal. This is achieved by using the REMs method described below, which should restore the user's hearing response to match that of a normal hearing profile and/or suit personal preferences with the hearing device inserted.

Figure 5:
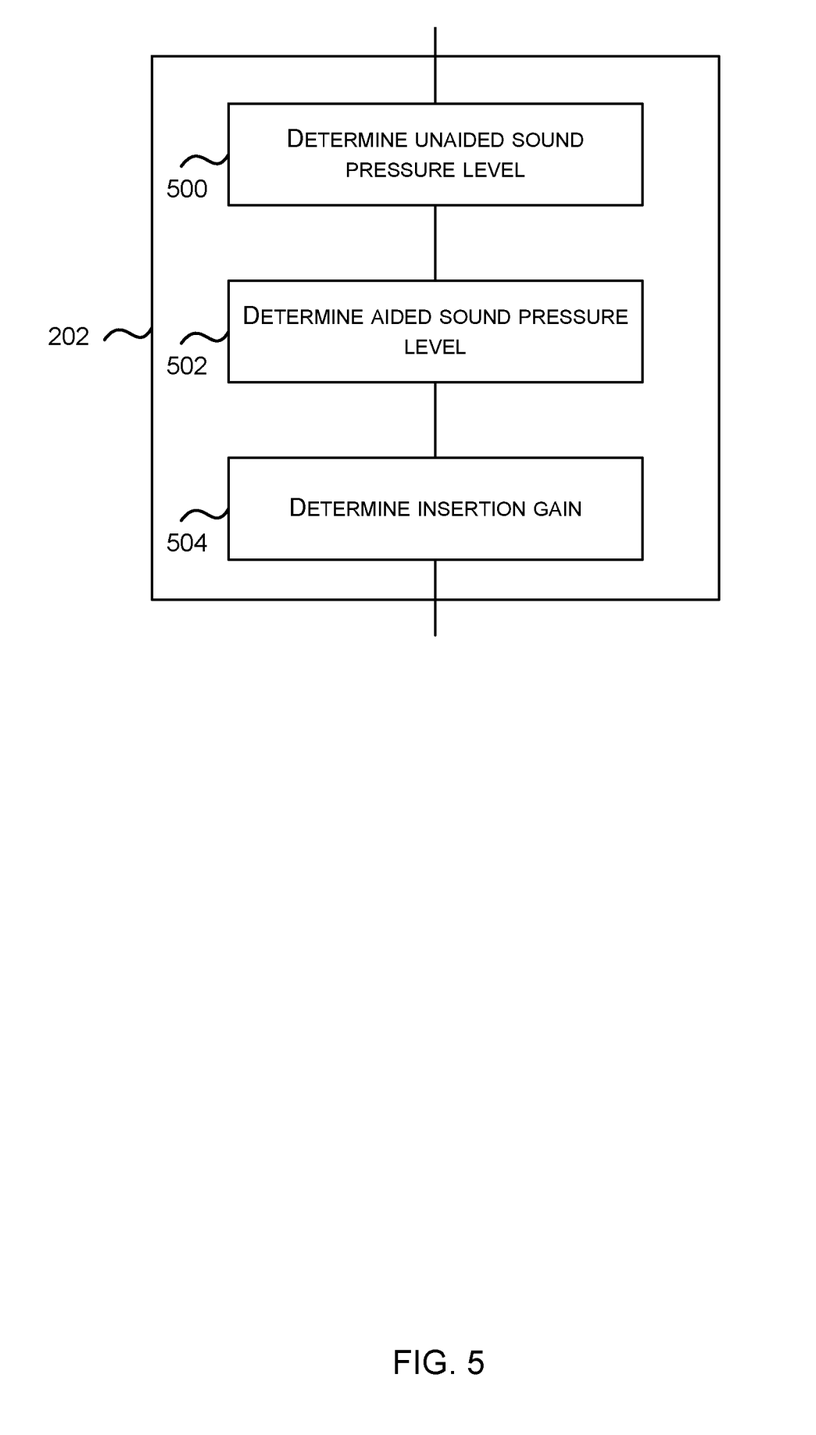
FIG. 5 shows a flow chart illustrating a method of determining an ear characteristic based on sound pressure levels.

FIG. 5 shows a flow chart illustrating a different example of the method of determining an ear characteristic, as in step 202 of FIG. 2. This method of determining an ear characteristic relies on the sound pressure level in the ear 9 of the user.

In step 500, the probe 25 and the sound pressure sensor 23 of the earpiece 3 measure the sound pressure level in the user's ear 9. Preferably the probe 25, which in this instance is a probe tube, is placed with its tip approximately 6 mm from the tympanic membrane of the ear 9. In this step the sound pressure level is measured when there is no audio stream output via the audio output device 7, or in other words when the audio output device 7 is inactive. This sound pressure level may be referred to as an unaided sound pressure level.

In step 502, as in step 500, the probe 25 and the sound pressure sensor 23 of the earpiece 3 measure the sound pressure level in the user's ear 9. However, in this step the sound pressure level is measured when the audio output device 7 is outputting the audio received by the external microphone 17 from the environment around the earpiece. Thus, in this step the sound pressure level is measured when the audio output device 7 is active. This sound pressure level may be referred to as an aided sound pressure level.

In step 504, the audio processing unit 11, 31 calculates the difference between the unaided sound pressure level and the aided sound pressure level in order to determine the 'insertion gain'. The insertion gain may be described as an ear characteristic. This characteristic can be matched to targets produced by various prescriptive formula based on the user's audiogram or individual hearing loss.

The size and shape of the ear canal affects the acoustics and resonant qualities of the ear. In "real-ear" the actual acoustic energy that exists within the ear canal of a particular person is accurately measured. Real-ear measurements (REMs) compare and verify the real-ear acoustic characteristics of a hearing device with a prescription target set by, for instance, a combination of OAE data, user preferences, and machine learning data.

Machine learning algorithms use audio sensing in diverse and unconstrained acoustic environments to adjust the user's listening experience according to a learned model based on a large dataset of place visits. Deepear is an example of micro-powered machine learning using deep neural networks (DNN) to significantly increase inference robustness to background noise beyond conventional approaches present in mobile devices. It uses computational models to infer a broad set of human behaviour and context from audio streams.

REMs allows the effects of hearing device fine tuning to be verified by taking into account any changes to the sound pressure level (SPL) of the signal caused by the shape of the ear. Fine tuning may include adjusting the overall volume, or making changes at specific pitches/frequencies.

A patient's real-ear unaided response (REUR), or in other words the natural "amplification" in the patient's open, or non-occluded, ear canal, ensures that a hearing device does not over-amplify in certain regions of the frequency response.

Real Ear Occluded Gain (REOG) is a measurement which involves the placement of the hearing device in the ear but muted/off. It allows consideration of the attenuation caused by the hearing device and its obstructing effect of external sounds and can be an indicator of the snugness of fit in the case of a hearing device which intends to diminish environmental sounds.

Figure 8A:
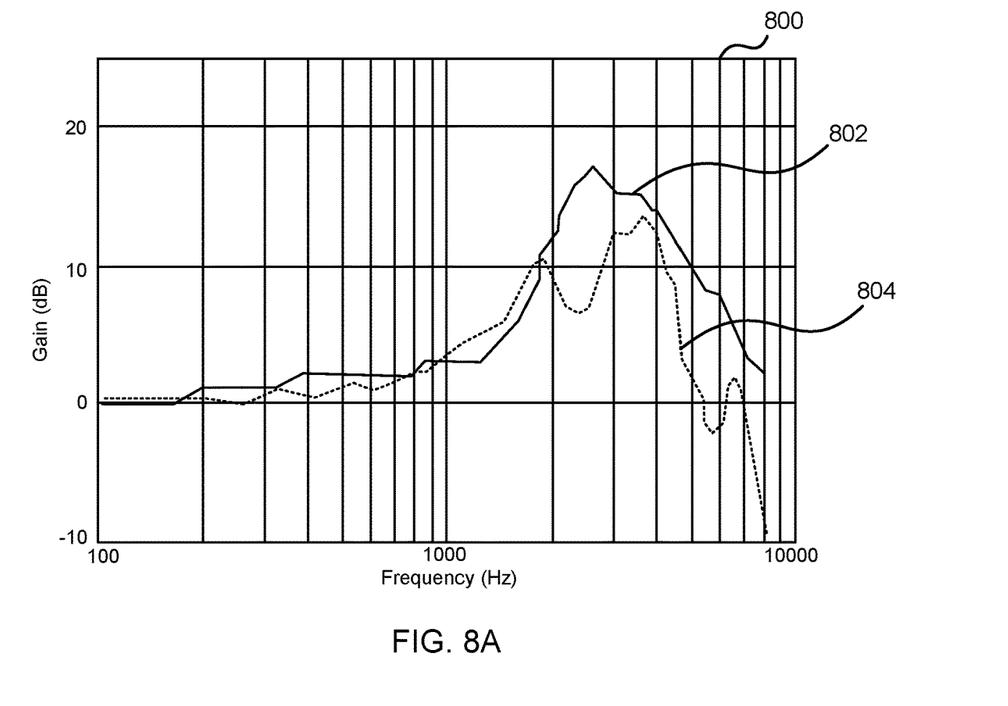
FIG. 8A illustrates a graph of a user's ear response to distortion product otoacoustic emissions (DPOAEs)

The existence of numerous resonance (gain) peaks in a real ear aided response (REAR) curve does not provide a smooth match to the prescriptive target. This is illustrated in the graph 800 shown in FIG. 8A, where line 802 shows the predicted gain and line 804 shows the real-ear gain.

Subtracting the level of the incoming signal from the REUR (real ear unaided response in dBs) gives a natural amplification or gain of the external ear (REUG—real ear unaided gain). This identifies any inherent resonance troughs caused by the external ear's acoustics for adjustment.

The insertion gain is the difference REAR−REUR (real ear aided response minus real ear unaided response in sound pressure levels) or REAG−REUG (real ear gain parameters). For good speech intelligibility in the presence of noise, especially the softer consonant components of speech, there needs to exist an SNR of at least 15 dB(A). The required insertion gain provided by the hearing device electronics improves an otherwise inadequate ear sensitivity characteristic such that softer sounds within the speech frequency spectrum are elevated to acceptable levels in preference to other sounds outside this range.

Figure 8B:
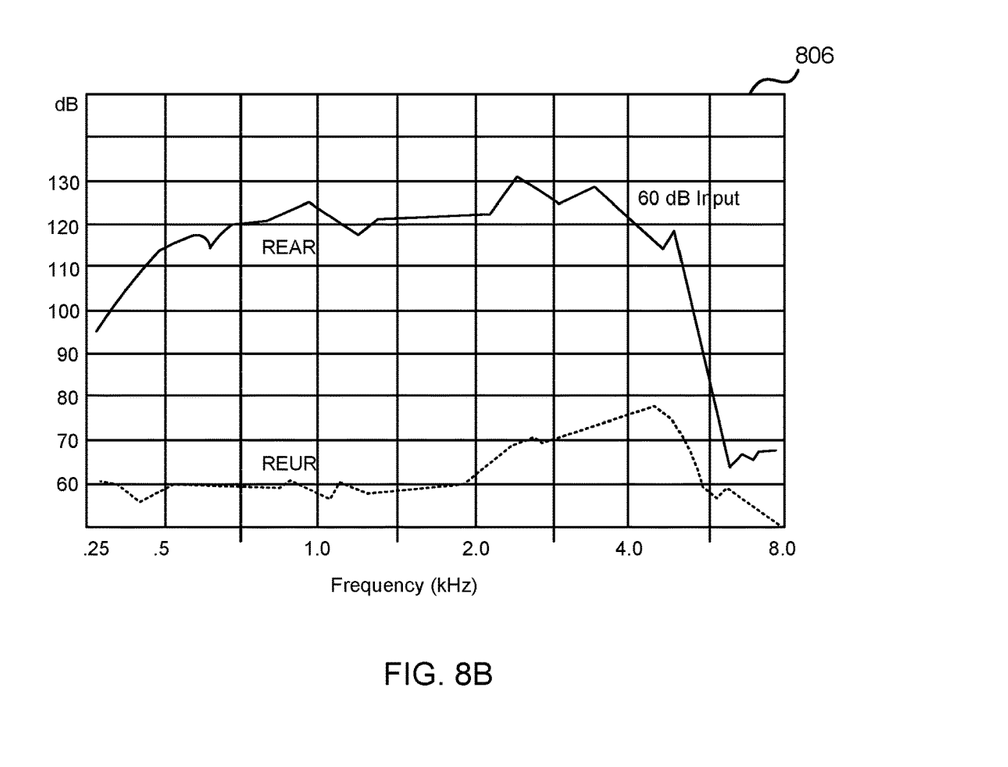
FIG. 8B illustrates a graph of a real ear aided response (REAR) and a real ear unaided response (REUR) for a hearing aid.

FIG. 8B illustrates a graph 806 of REAR and REUR readings for a hearing aid that has been "acoustically matched" to an individual patient's ear. This is shown by the smooth real-ear aided response (REAR), particularly between 2000 and 4000 Hz.

Figure 6:
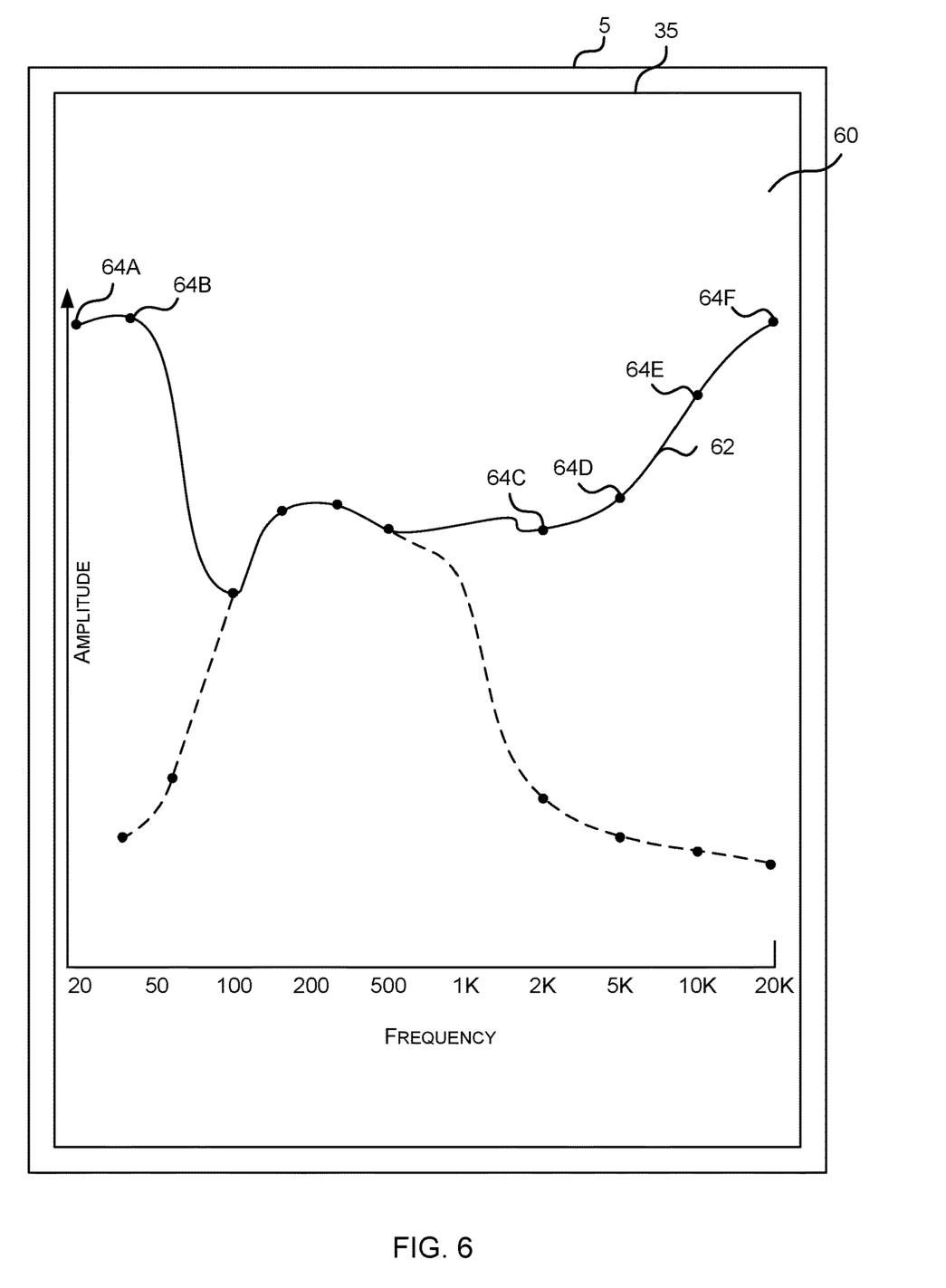
FIG. 6 illustrates an example of a display in an audio streaming mode of the assembly.

FIG. 6 illustrates an example of the display 35 of the computing device 5 when the audio processing unit 11, 31 is in the audio streaming mode. In this example, the touch screen display 35 presents a graph 60 to the user. A first line 62 on the graph 60 displays the constituent frequencies within the sound from the environment received via the external microphone 17, along with the amplitude of each of the frequencies.

The user can select points 64A-F along the first line 62 using the touch-screen display 35. Once one of the points 64A-F has been selected the user can drag that point to a desired amplitude.

In one hypothetical example, the user may be listening to the sounds in the surrounding environment using the earpiece 3 via the audio output device 7, and there may be a repetitive and loud low-frequency noise in the audio stream. This noise may be hindering the user's ability to hear a person speak. In response, the user may select points 64A and 64B and drag them down in order to reduce their amplitude so that the noise is less prominent in the audio stream.

In another hypothetical example, there may be an undesired high frequency noise in the audio stream from the environment. In response, the user may select points 64C-F and drag them down in order to reduce their amplitude so that the high frequency noise is less prominent in the audio stream.

In re-arranging points 64A-F the user has created a second line, which represents the actual output of the audio output device 7, and the graph 60 displays the difference between the actual sounds in the environment in comparison to the sounds output via the earpiece. In adjusting the audio stream a user will be able to highlight sounds that they want to hear and diminish sounds that they do not want to hear. This helps to optimise the user's listening experience. The user's listening experience is optimised further by adjusting the audio stream based on the ear characteristic determined in the hearing test mode. In another example, the computing device 5 may select audio having a particular frequency above a certain threshold and lower the amplitude of the selected audio automatically, without intervention from the user.

In another example, the computing device 5 may be arranged to receive an input from a user indicating a preferred frequency response for the audio stream output in the audio streaming mode.

For instance, the user may be able to adjust a graphic equaliser presented via the touch screen display. The audio processing unit may be arranged to adjust the output of the audio stream in the audio streaming mode based on the at least one ear characteristic determined in the hearing-test mode and the preferred frequency response indicated by the user. Therefore, it is possible to optimise the audio stream based on a combination of user preferences and results of the hearing test. Therefore, the user may be able to 'fine-tune' their listening experience in order to achieve the optimum audio stream.

Figure 7A:
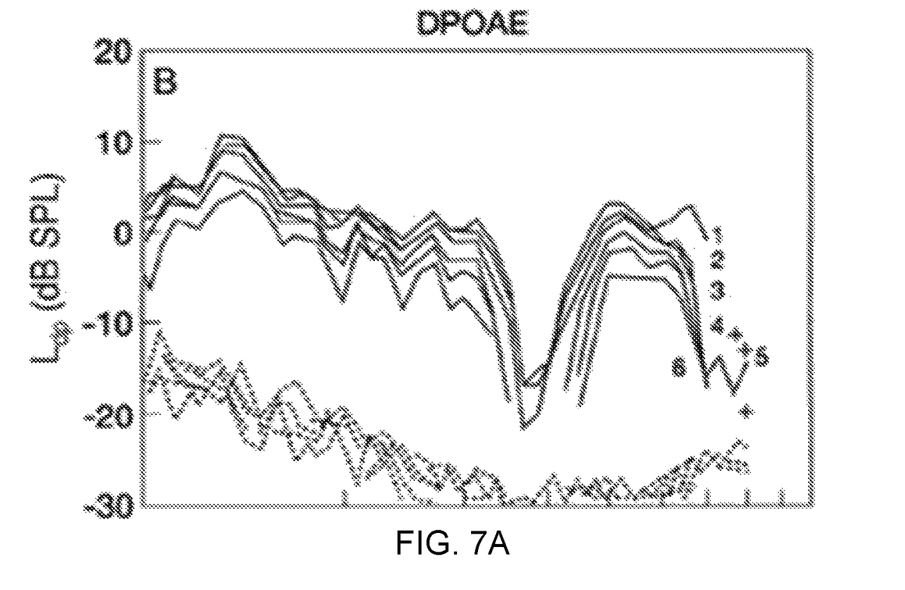
FIGS. 7A and 7B illustrate an example of a user's hearing profile.
Figure 7B:
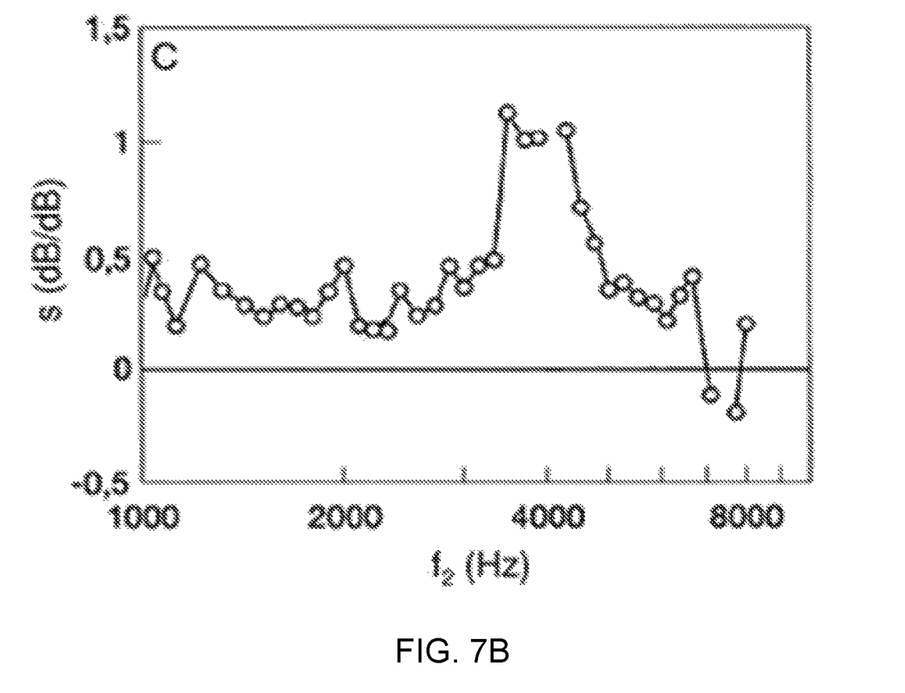

FIG. 7A and FIG. 7B illustrate an example of a user's hearing profile. The user's measured hearing profile is compared to a range of reference values within which normal hearing is considered to lie. In the hearing profile below, it can be seen that the DPOAE measurements in FIG. 7A correlate closely with the audiometric profile in FIG. 7B of a hearing loss patient. There is also good correlation with TOAE data, which is not illustrated here. In this example, the noise floor is the lower curve in FIG. 7A, and the notch in the curve indicating hearing loss lies near the 15 dB threshold. From this data notches in the user's hearing profile can be optimised by adding the correct amount of insertion gain into the hearing device electronics at those frequencies, as previously described.

The methods described herein may be performed by software in machine readable form on a tangible storage medium e.g. in the form of a computer program comprising computer program code means adapted to perform all the steps of any of the methods described herein when the program is run on a computer and where the computer program may be embodied on a computer readable medium. Examples of tangible (or non-transitory) storage media include disks, thumb drives, memory cards etc and do not include propagated signals. The software can be suitable for execution on a parallel processor or a serial processor such that the method steps may be carried out in any suitable order, or simultaneously. This acknowledges that firmware and software can be valuable, separately tradable commodities. It is intended to encompass software, which runs on or controls "dumb" or standard hardware, to carry out the desired functions. It is also intended to encompass software which "describes" or defines the configuration of hardware, such as HDL (hardware description language) software, as is used for designing silicon chips, or for configuring universal programmable chips, to carry out desired functions.

The term 'computer' or 'computing device' is used herein to refer to any device with processing capability such that it can execute instructions. Those skilled in the art will realise that such processing capabilities are incorporated into many different devices and therefore the term 'computer' or 'computing device' includes PCs, servers, mobile telephones, personal digital assistants and many other devices.

Those skilled in the art will realise that storage devices utilised to store program instructions can be distributed across a network. For example, a remote computer may store an example of the process described as software. A local or terminal computer may access the remote computer and download a part or all of the software to run the program. Alternatively, the local computer may download pieces of the software as needed, or execute some software instructions at the local terminal and some at the remote computer (or computer network). Those skilled in the art will also realise that by utilising conventional techniques known to those skilled in the art that all, or a portion of the software instructions may be carried out by a dedicated circuit, such as a DSP, programmable logic array, or the like.

Any range or device value given herein may be extended or altered without losing the effect sought, as will be apparent to the skilled person.

It will be understood that the benefits and advantages described above may relate to one embodiment or may relate to several embodiments. The embodiments are not limited to those that solve any or all of the stated problems or those that have any or all of the stated benefits and advantages.

Any reference to 'an' item refers to one or more of those items. The term 'comprising' is used herein to mean including the method blocks or elements identified, but that such blocks or elements do not comprise an exclusive list and a method or apparatus may contain additional blocks or elements.

The steps of the methods described herein may be carried out in any suitable order, or simultaneously where appropriate. Additionally, individual blocks may be deleted from any of the methods without departing from the spirit and scope of the subject matter described herein. Aspects of any of the examples described above may be combined with aspects of any of the other examples described to form further examples without losing the effect sought. Any of the module described above may be implemented in hardware or software.

It will be understood that the above description of a preferred embodiment is given by way of example only and that various modifications may be made by those skilled in the art. Although various embodiments have been described above with a certain degree of particularity, or with reference to one or more individual embodiments, those skilled in the art could make numerous alterations to the disclosed embodiments without departing from the scope of this invention.

The invention claimed is:

1. An auditory device assembly comprising:
an earpiece for obstructing external sounds, the earpiece having:

an audio output device for providing sound to an ear of a user;

an ear microphone for detecting sound emitted by the ear of the user;

an external microphone for receiving sound signals from an environment outside the earpiece; and a storage module for recording an ear characteristic of the user's ear; and an audio processing unit having:

a hearing-test mode in which the audio processing unit is arranged to determine at least one ear characteristic of the ear of the user based on at least one hearing test; and an audio streaming mode in which the audio processing unit is arranged to output an audio stream via the audio output device;

wherein the at least one hearing test comprises detecting one or more Spontaneous Otoacoustic Emissions (SOAEs) from the ear of the user, without external stimulation of the ear of the user; monitoring the SOAEs over time; and identifying the onset of hearing impairment based on the detected SOAEs.

2. The auditory device assembly according to claim 1, wherein the audio processing unit is arranged to adjust the output of the audio stream in the audio streaming mode based on the at least one ear characteristic determined in the hearing-test mode; and the at least one ear characteristic represents the sensitivity of the ear to at least one frequency, wherein the audio processing unit is arranged to adjust the output of the audio stream based on the sensitivity of the ear to at least one frequency, so that a frequency to which the ear is less sensitive is amplified and/or a frequency to which the ear is more sensitive is attenuated.

3. The auditory device assembly according to claim 1, wherein the audio processing unit is arranged, in the hearing-test mode, to determine at least one ear characteristic of the ear based on sound emitted by the ear of the user detected by the ear-microphone.

4. The auditory device assembly according to claim 1, wherein the audio processing unit is arranged, in the hearing-test mode, to determine at least one ear characteristic of the ear based on an Evoked Otoacoustic Emission (EOAE) response detected by the ear-microphone in response to at least one pre-defined audio test signal;

wherein the at least one pre-defined audio test signal is selected based on the detected SOAEs.

5. The auditory device assembly according to claim 1, further comprising:

an audio-microphone arranged to receive audio input from the environment surrounding the earpiece;

wherein the audio stream output via the audio output device comprises at least a part of the audio input from the environment.

6. The auditory device assembly according to claim 5, further comprising:

a pressure sensor arranged to measure an aided and/or unaided sound pressure level in the ear of the user when the audio output device is outputting the audio streaming comprising at least a part of the audio input from the environment, wherein the audio processing unit, in the hearing test mode, is arranged to determine the difference between the aided sound pressure level and the unaided sound pressure level, in order to determine the at least one ear characteristic.

7. The auditory device assembly according to claim 1, further comprising:

a user interface device arranged to receive an input from a user indicating a preferred intensity of at least one frequency of the audio stream in the audio streaming mode;

wherein the audio processing unit is arranged to adjust the output of the audio stream in the audio streaming mode based on the at least one ear characteristic determined in the hearing-test mode and the preferred frequency response indicated by the user.

8. The auditory device assembly according to claim 1, further comprising:

a storage device arranged to store the at least one ear characteristic determined in the hearing-test mode;

wherein the earpiece comprises the storage device;

wherein the storage module is connected remotely to the earpiece; and wherein a server comprises the storage module.

9. The auditory device assembly according to claim 1, wherein the audio processing unit is arranged to operate in the hearing-test mode and the audio streaming mode concurrently.

10. The auditory device assembly according to claim 1, further comprising:

an audio-microphone arranged to receive audio input from the environment surrounding the earpiece;

an audio processing unit arranged to identify the magnitude of respective frequencies in the audio input;

a display arranged to present the magnitude of respective frequencies identified in the audio input; and a user interface arranged to receive an input from a user indicating a preferred magnitude of at least one of the respective frequencies;

wherein the audio processing unit is arranged, in the audio streaming mode, to output an audio stream via the audio output device, that is adjusted based on the preferred magnitude indicated by the user.

11. The auditory device assembly according to claim 1, wherein the hearing-test mode further comprises:

comparing two or more SOAEs; and identifying the onset of hearing impairment based on the detected SOAEs comprises identifying changes in the user's SOAE profile.

12. The auditory device assembly according to claim 11, wherein identifying the onset of hearing impairment further includes monitoring the attenuation over time of SOAE narrow-band frequency spikes indicating reduced sensitivity of the ear to at least one frequency.

13. The auditory device assembly according to claim 1, wherein the hearing test mode further comprises initiating a specific EOAE hearing test if hearing impairment is detected.

14. The auditory device assembly according to claim 1, wherein the audio processing unit is arranged to identify the frequencies affected by changes in the user's SOAE profile, and:

implement evoked otoacoustic emission (EOAE) tests based on those affected frequencies and adjust the audio stream settings accordingly;

adjust the audio stream settings according to historical EOAE test data from comparable SOAE characteristics; and/or adjust the audio stream settings based on the attenuation of SOAE narrow-band frequency spikes.

15. An audio processing unit having:

a storage module for recording an ear characteristic of an ear of a user;

an audio streaming mode in which the audio processing unit is arranged to output an audio stream via an audio output device of an earpiece for the ear of the user; and a hearing-test mode in which the audio processing unit is arranged to determine at least one ear characteristic of the ear of the user based on at least one hearing test; and wherein the at least one hearing test comprises monitoring Spontaneous Otoacoustic Emissions (SOAEs) over time, detected without external stimulation of the ear; and identifying the onset of hearing impairment based on the detected SOAEs.

16. A method comprising:

determining at least one ear characteristic of an ear of a user, using an audio processing unit in a hearing-test mode and an ear-microphone arranged to detect sound emitted by the ear of the user;

wherein detecting the sound comprises obstructing external sounds to detect one or more Spontaneous Otoacoustic Emissions (SOAEs) without external stimulation of the ear of the user;

recording said ear characteristic of the ear of the user in a storage module;

monitoring the detected SOAEs over time;

identifying the onset of hearing impairment based on the detected SOAEs; and outputting an audio stream via an audio output device of an earpiece for an ear of a user, using the audio processing unit in an audio streaming mode.

17. The method according to claim 16, wherein the audio streaming mode further comprises the step of adjusting the output of the audio stream, using the audio processing unit based on the at least one ear characteristic determined in the hearing-test mode; and the at least one ear characteristic represents the sensitivity of the ear to at least one frequency, wherein adjusting the output of the audio stream comprises adjusting the output of the audio stream based on the sensitivity of the ear to at least one frequency, so that a frequency to which the ear is less sensitive is amplified and/or a frequency to which the ear is more sensitive is attenuated.

18. The method according to claim 16, further comprising:

determining at least one ear characteristic of the ear based on an Evoked Otoacoustic Emission (EOAE) response detected by the ear-microphone in response to at least one pre-defined audio test signal;

wherein the at least one pre-defined audio test signal is selected based on the detected SOAEs.

19. The method according to claim 16, further comprising:

receiving audio input from the environment surrounding the ear piece via an audio-microphone;

outputting the audio stream via the audio output device, the audio stream comprising at least a part of the audio input from the environment.

20. The method according to claim 19, further comprising:

measuring, using a pressure sensor, an aided and/or unaided sound pressure level in the ear of the user when the audio output device is outputting the audio stream comprising at least a part of the audio input from the environment, wherein the audio processing unit, in the hearing test mode, is arranged to determine the difference between the aided sound pressure level and the unaided sound pressure level, in order to determine the at least one ear characteristic.

21. The method according to claim 16, further comprising:

receiving an input from a user indicating a preferred intensity of at least one frequency of the audio stream in the audio streaming mode; and adjusting the output of the audio stream in the audio streaming mode based on the at least one ear characteristic determined in the hearing-test mode and the preferred frequency response indicated by the user.

22. The method according to any claim 16, further comprising:

storing, at a storage device, the at least one ear characteristic determined in the hearing-test mode.

23. The method according to claim 16, further comprising operating the audio processing unit in the hearing-test mode and the audio streaming mode concurrently.

24. The method according to claim 16, further comprising:

receiving, at an audio-microphone, audio input from the environment surrounding the earpiece;

displaying, at a display, the magnitude of respective frequencies in the audio input; and receiving, at a user interface, an input from a user indicating a preferred magnitude of at least one of the respective frequencies; and outputting, using the audio processing unit in the audio streaming mode, an audio stream via the audio output device, that is adjusted based on the preferred magnitude indicated by the user.

* * * * *